United States Patent
Basu et al.

(10) Patent No.: US 7,551,708 B2
(45) Date of Patent: Jun. 23, 2009

(54) METHOD OF ITERATIVE RECONSTRUCTION FOR ENERGY DISCRIMINATING COMPUTED TOMOGRAPHY SYSTEMS

(75) Inventors: Samit Kumar Basu, Niskayuna, NY (US); Bruno Kristiaan Bernard DeMan, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 61 days.

(21) Appl. No.: 11/672,137

(22) Filed: Feb. 7, 2007

(65) Prior Publication Data

US 2008/0187091 A1  Aug. 7, 2008

(51) Int. Cl.
*A61B 6/00* (2006.01)

(52) U.S. Cl. .......................................................... 378/5

(58) Field of Classification Search .................. 378/4, 378/5, 53, 88
See application file for complete search history.

(56) References Cited

U.S. PATENT DOCUMENTS

| | | | | |
|---|---|---|---|---|
| 4,029,963 A | * | 6/1977 | Alvarez et al. | 378/5 |
| 4,217,641 A | * | 8/1980 | Naparstek | 382/131 |
| 4,626,991 A | * | 12/1986 | Crawford et al. | 378/4 |
| 4,633,398 A | * | 12/1986 | Gullberg et al. | 382/270 |
| 4,751,722 A | * | 6/1988 | Harding et al. | 378/6 |
| 5,039,856 A | * | 8/1991 | Tron | 250/358.1 |
| 5,155,365 A | * | 10/1992 | Cann et al. | 250/363.02 |
| 5,438,202 A | * | 8/1995 | Matanzon et al. | 250/363.07 |
| 5,838,758 A | * | 11/1998 | Krug et al. | 378/53 |
| 6,016,333 A | * | 1/2000 | Kalvin | 378/4 |
| 6,018,562 A | * | 1/2000 | Willson | 378/9 |
| 6,507,633 B1 | | 1/2003 | Elbaki et al. | |
| 6,724,856 B2 | * | 4/2004 | DeMan et al. | 378/62 |
| 6,754,298 B2 | | 6/2004 | Fessler | |
| 2003/0072409 A1 | * | 4/2003 | Kaufhold et al. | 378/53 |
| 2003/0103666 A1 | * | 6/2003 | Edic et al. | 382/132 |
| 2004/0264627 A1 | * | 12/2004 | Besson | 378/5 |
| 2005/0259784 A1 | * | 11/2005 | Wu et al. | 378/19 |
| 2006/0067461 A1 | * | 3/2006 | Yin et al. | 378/5 |

* cited by examiner

*Primary Examiner*—Edward J Glick
*Assistant Examiner*—Alexander H Taningco
(74) *Attorney, Agent, or Firm*—Global Patent Operation

(57) ABSTRACT

A new method extends iterated coordinate descent ("ICD")—an optimization method employed in some statistical reconstruction algorithms—to handle material decomposition ("MD") for energy discriminating computed tomography ("EDCT") acquisitions.

8 Claims, 3 Drawing Sheets

METHOD OF ITERATIVE RECONSTRUCTION FOR ENERGY DISCRIMINATING COMPUTED TOMOGRAPHY SYSTEMS

BACKGROUND

1. Field of the Invention

The present disclosure relates to computed tomography ("CT") systems generally, and more particularly, to a method for applying iterated coordinate descent ("ICD") to handle material decomposition ("MD") for energy discriminating computed tomography ("EDCT") acquisitions.

2. Description of Related Art

CT systems are now becoming available that collect data using multiple spectra (i.e., multiple kVPs or multiple filtrations) or that collect data using energy discriminating detectors (e.g., layered energy integrating detectors or photon counting detectors). In such configurations, the collected data contains information about the material composition of the scanned object. This information is typically expressed as the atomic number or as the photoelectric and Compton components of the scanned object.

Known reconstruction algorithms take these indirect line-integral measurements and create volumetric representations of the object from which detection or diagnosis can take place. Additionally, it is known that iterative and statistical reconstruction techniques outperform non-iterative techniques in creating the volumetric representations. In particular, for the same resolution iterative and/or statistical methods can show a significant reduction in image noise. We refer to reconstruction algorithms (iterative, statistical or otherwise) that use a polychromatic spectrum without energy discrimination capability to be "polychromatic" algorithms. This includes, for example, the state of the art in iterative and non-iterative reconstruction.

For example, traditional iterated coordinate descent ("ICD"), used in either 2D or 3D variants to reconstruct X-ray attenuation for a pixel, involves:

1. forming an initial image;
2. performing a sequence of iterations;
3. for each iteration, visiting each of the pixels in the image in turn; and
4. for each pixel visited with an iteration, replacing the pixel's scalar value with a new scalar value, which is computed by optimizing a cost function on the image as a whole, where all other pixels in the image are fixed at an estimated scalar value.

Consequently, only a single component needs be determined, and that is the new scalar value for each pixel visited with an iteration.

What is needed is a novel extension of polychromatic iterative and/or statistical reconstruction methods to handle the multiple energy data collected by an energy discriminating computed tomography ("EDCT") system.

BRIEF SUMMARY OF THE INVENTION

The present disclosure describes a new method that overcomes the disadvantages associated with the related art and meets the needs discussed above. In general, an embodiment of the new method extends iterated coordinate descent ("ICD")—an optimization method employed in some statistical reconstruction algorithms—to handle material decomposition ("MD") for energy discriminating computed tomography ("EDCT") acquisitions. Advantages afforded by embodiments of the new method include faster processing times a final component image having low noise, better separation of the material components than traditional direct techniques, increased robustness to data quality problems, reduced image domain artifacts, and the incorporation of a priori information into the reconstruction.

Other features and advantages of the disclosure will become apparent by reference to the following description taken in connection with the accompanying drawings.

BRIEF DESCRIPTION OF THE DRAWINGS

Reference is now made briefly to the accompanying drawings, in which.

Like reference characters designate identical or corresponding components and units throughout the several views.

DETAILED DESCRIPTION

Figure 1:
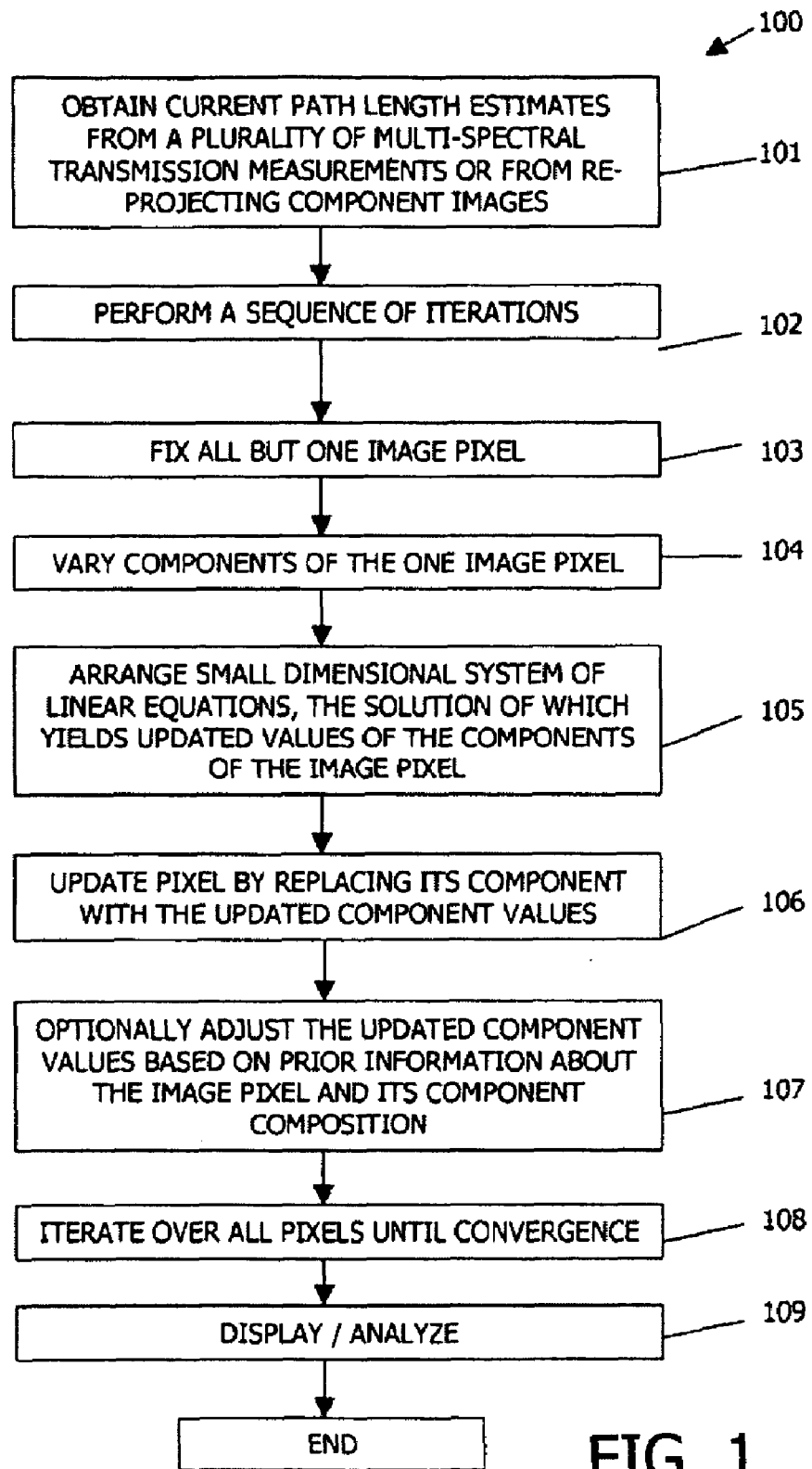
FIG. 1 is a flowchart illustrating an embodiment of a new method of extending iterated coordinate descent to an energy discriminating computed tomography ("EDCT") system.

FIG. 1 is a flowchart of an embodiment of a new method 100 of extending iterated coordinate descent ("ICD")—an optimization method employed in some statistical reconstruction algorithms—to handle material decomposition ("MD") for energy discriminating computed tomography ("EDCT") acquisitions.

For example, as mathematically explained below, embodiments of the invention provide the following modifications to traditional ICD. The method 100 may include a step 101 of obtaining current path length estimates, which are mathematical calculations to compute the amount of attenuation that multi-spectra x-rays experience as they pass through a scannable object. In general, the current path length estimates may be obtained from multi-spectral acquisition data detected by a detector of an EDCT system. More particularly, as a skilled artisan will appreciate, the path length estimates may be calculated using known Material Decomposition techniques on line integrals obtained from raw EDCT measurements (e.g., from two or more sinograms). In other words, an embodiment of step 101 comprises decomposing an energy-discriminating computed tomography ("EDCT") image onto a fixed set of basis components to produce a set of images.

The scannable object may be anything capable of being scanned by an energy discriminating computed tomography ("EDCT") system. Non-limiting examples of a scannable object include any type of human or animal anatomy, geologic materials (e.g., petrochemical rock characterization, soil analysis, etc.), pieces of passenger baggage (for explosive detection purposes), manmade objects (for non-destructive evaluation purposes), and the like.

As mathematically described below, the method 100 may further include a step 102 of performing a sequence of iterations on the set of images. The sequence of iterations may include one or more of steps 103, 104, 105, 106, 107, 108, and

109. At step 103, all image pixels, save one, are fixed at estimates of their scalar values. In other words, the method 100 further comprises fixing 109 all but one image pixel at an estimated scalar value. At step 104, the coordinates of the one pixel are varied (or allowed to vary). In other words, the method 100 comprises varying 104 at least one component value of the one image pixel. Unlike the traditional ICD case (where a single scalar value is associated with each pixel), there are now several component values for each pixel that need to be updated; and the number of component values depends on the number of images in the set of images.

The method 100 may further include a step 105 of arranging a small dimensional system of linear equations, the solution of which yields updated values of the components of the one image pixel. In an embodiment, "small dimensional" refers to a 2×2 matrix equation, but other dimensional matrix equations are possible. For example, if K-edge materials are present in the object being scanned, then each image pixel may have more than two components. In general if N components are required for each pixel, then the matrix equation could be N×N. In other words, the method 100 further comprises solving 105 a system of linear equations to obtain at least one updated component value of the one image pixel.

At step 106, the pixel is updated based on its current values and on the updated component values. In other words, method 100 comprises replacing 106 the at least one component value of the one image pixel with the at least one updated component value, which was obtained from step 105. Optionally, at step 107, the method 100 may include (optionally) adjusting the at least one updated component value based on prior information about the one image pixel and its component composition. At step 108, the image is iterated over all pixels until convergence (e.g., the method steps 103, 104, 105, 106 and/or 107 are repeated for each image pixel until convergence occurs). In other words, the method 100 further comprises iterating 108 over all image pixels until convergence. At step 109, the optimized, converged image may be displayed and/or analyzed. In other words, method 100 further comprises displaying 109 an optimized converged image.

In an embodiment, the FIG. 1 flow chart steps are implemented in a microprocessor and associated memory elements within an EDCT system. In such an embodiment the FIG. 1 steps represent a program stored in the memory element and operable in the microprocessor. When implemented in a microprocessor, program code configures the microprocessor to create logical and arithmetic operations to process the flow chart steps. The FIG. 1 flow chart steps may also be embodied in the form of computer program code written in any of the known computer languages containing instructions embodied in tangible media such as floppy diskettes, CD-ROM's, hard drives, DVD's, removable media or any other computer-readable storage medium. When the program code is loaded into and executed by a general purpose or a special purpose computer, the computer becomes an apparatus for practicing embodiments of the invention. The FIG. 1 flow chart steps can also be embodied in the form of a computer program code, for example, whether stored in a storage medium loaded into and/or executed by a computer or transmitted over a transmission medium, such as over electrical wiring or cabling, through fiber optics, or via electro-magnetic radiation, wherein when the computer program code is loaded into and executed by a computer, the computer becomes an apparatus for practicing the embodiments of the invention.

Figure 2:
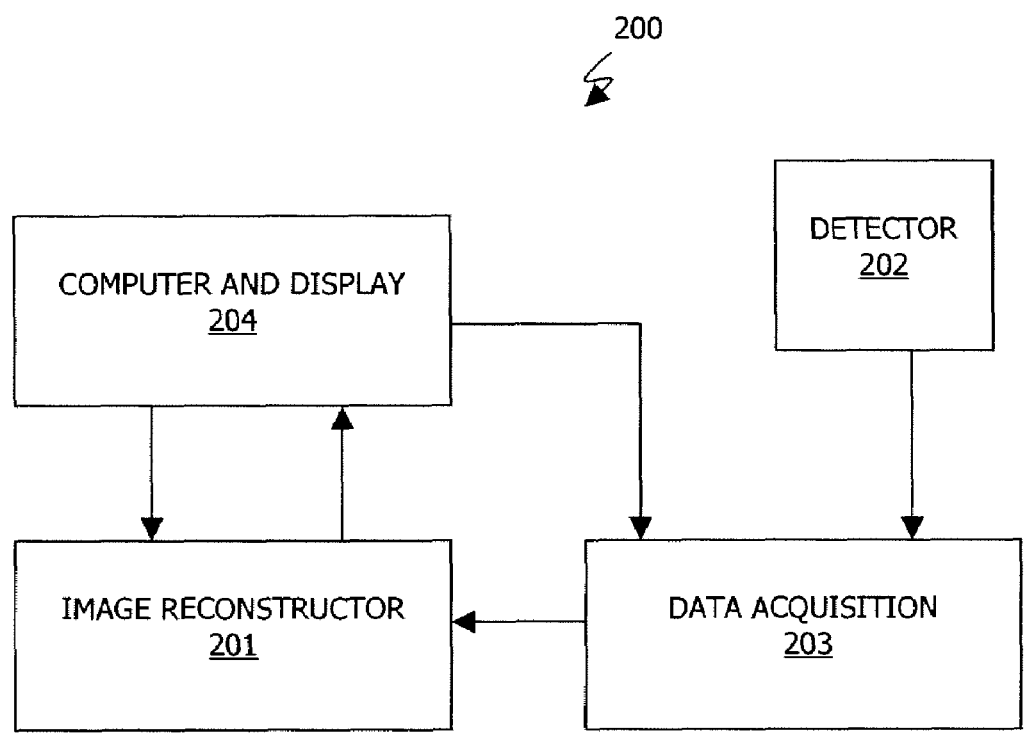
FIG. 2 is a simplified schematic block diagram of a reconstruction apparatus for use in an EDCT system to perform embodiments of the new method illustrated in the flowchart of FIG. 1.

FIG. 2 is a simplified schematic block diagram 200 illustrating how an image reconstructor 201 interacts with a CT detector 202, a data acquisition module 203, and a computer/display 204 to perform embodiments of the method 100 of FIG. 1. Each of the components 201, 202, 203, and 204 shown in FIG. 2 may be part of an EDCT system, or subsystem thereof.

Figure 3:
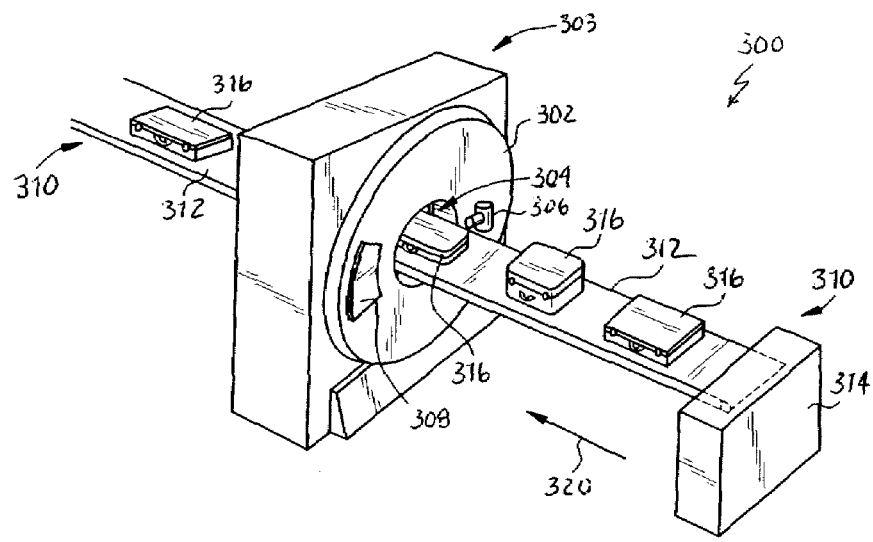
FIG. 3 is a perspective view of an exemplar x-ray based inspection system, which may be configured to perform embodiments of the method illustrated in the flowchart of FIG. 1.
Figure 4:
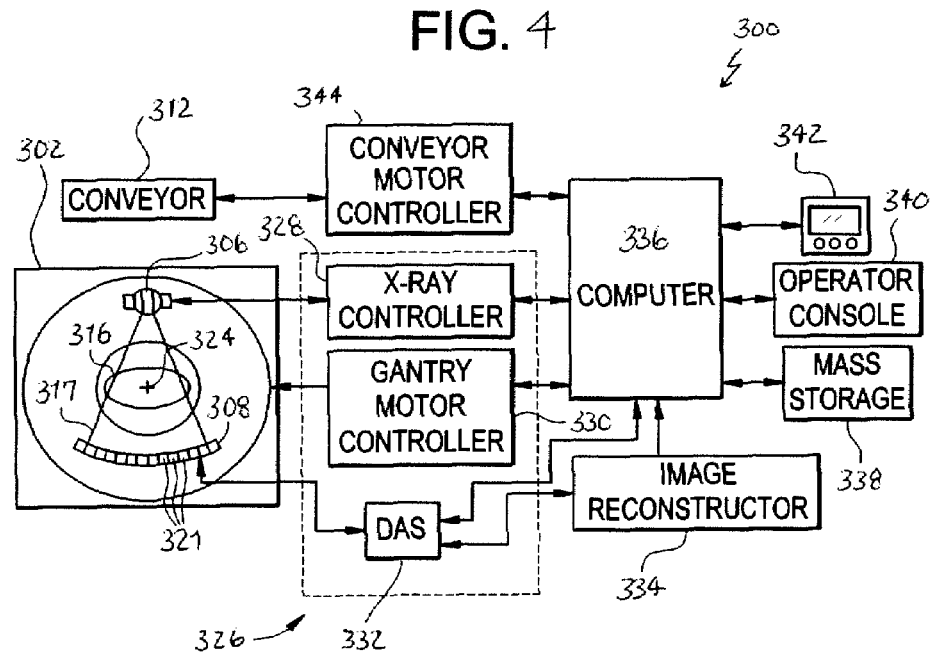
FIG. 4 is a block schematic diagram of the exemplary x-ray inspection system of FIG. 3.

FIGS. 3 and 4 illustrate an exemplary type of an EDCT inspection system 300 that may be configured to perform embodiments of the method illustrated in the flowchart of FIG. 1, and further described below. The inspection system 300 may be an explosive detection system (or a medical inspection system) that includes an x-ray EDCT scanner 303.

The rotatable gantry 302 has an opening 304 therein, through which scannable objects 316 may pass. A non-limiting example of a type of scannable object is passenger baggage, but other types of scannable objects such as a medical patient, manmade and natural objects, and the like are also contemplated. The rotatable gantry 302 houses an x-ray source 306 as well as a detector assembly 308 having scintillator arrays comprised of scintillator cells. A conveyor system 310 is also provided. The conveyor system 310 includes a conveyor belt 312 supported by structure 314 to automatically and continuously pass objects 316 to be scanned through opening 304. Directional arrow 320 indicates the direction in which the conveyor belt 312 rotates. In an alternative embodiment, the conveyor system 310 may be replaced with a movable table (not shown) configured to move a medical patient in and/or out of the opening 304.

Objects 316 are fed into the opening 304 by conveyor belt 312 (or a movable table). Imaging data is then acquired and reconstructed. Embodiments of the method illustrated in the flowchart of FIG. 1 may be used to perform the image reconstruction. As a result, human operators of the EDCT inspection system 300 may non-invasively inspect the contents of scannable objects 316 for items of interest. The term "items or interest" refers to any substance or thing that the EDCT inspection system 300 is configured to detect. Non-limiting examples of "items of interest" include explosives, illegal drugs, hazardous substances, product components, medical ailments, and the like. Additional aspects of the inspection system 300 are described below with reference to FIGS. 3 and 4.

FIG. 4 is a block schematic diagram of the EDCT inspection system 300 of FIG. 3. Referring to FIGS. 3 and 4, the EDCT inspection system 300 includes a circular, movable gantry 302. An x-ray source 306 attached to the gantry 302 projects a fan (or cone) beam of x-rays 317 across the interior of the gantry 302 to a detector array 308 that is also attached to the gantry 302. The detector array 308 is formed by a plurality of detector modules 321, which together sense the projected x-rays that pass through an object 316. Each detector module 321 comprises an array of pixel elements (pixels). Each pixel comprises in part a photosensitive element, such as a photodiode, and one or more charge storage devices, such as capacitors. Each pixel produces an electrical signal that represents the intensity of an impinging x-ray beam and hence the attenuated beam as it passes through the object 316. During a scan to acquire x-ray projection data, gantry 302 and the components mounted thereon rotate about a center of rotation 324.

Rotation of gantry 302 and the operation of x-ray source 306 are governed by a control mechanism 326 of the inspection system 300. Control mechanism 326 includes in x-ray controller 328 that provides power and timing signals to an x-ray source 306 and a gantry motor controller 330 that controls the rotational speed and position of gantry 302. A data acquisition system (DAS) 332 in control mechanism 326 samples analog data from detectors 321 and converts the data to digital signals for subsequent processing. An image reconstructor 334 receives sampled and digitized x-ray data from DAS 332 and performs high-speed reconstruction using an embodiment of the method illustrated in the flowchart of FIG. 1 and further described below. The reconstructed image is applied as an input to a computer 336, which stores the image in a mass storage device 338.

Computer 336 also receives commands and scanning parameters from an operator via console 340 that has a keyboard. An associated display 342 allows the operator to observe the reconstructed image and other data from computer 336. The operator supplied commands and parameters that are used by computer 336 to provide control signals and information to DAS 332, x-ray controller 328, and gantry motor controller 330. In addition, computer 336 operates a conveyor motor controller 344, which controls a conveyor belt 312 to position object 316 within the gantry 302. Particularly, conveyor belt 312 moves portions of the object 516 through the gantry opening 304.

There are a number of new ways to extend monoenergetic ICD techniques to handle the polychromatic EDCT case. Furthermore there are a number of definitions of EDCT depending on the nature of the scanner involved. In this disclosure the exact nature of the energy-discriminating data is irrelevant, only that there are multiple spectral measurements, and that for each spectrum the response of the system is either known or characterizable. The basis for the classic ICD algorithm is that a one-dimensional line search can be computed quite efficiently as Equation (1):

$$x^{k+1} = x^k + \alpha^k \delta_i | \quad (1)$$

where $\delta_i$ is the basis function for the ith pixel, and $\alpha$ is chosen to minimize the penalized weighted least squares (PWLS) cost function as Equation (2):

$$\alpha^k = \underset{\alpha}{\operatorname{argmin}} \|A(x^k + \alpha \delta_i) - b\|_2^2 + \lambda \phi(x^k + \alpha \delta_i) \quad (2)$$

where $\lambda$ is a regularization parameter, and o is a penalty or prior term. For the case of no penalty (with a simple modification for the quadratic penalty case), the solution for $\alpha$ can be found in closed form as Equation (3):

$$\alpha = \frac{\langle A\delta_t, Ax^k - b \rangle}{\|A\delta_i\|_2^2} \quad (3)$$

The exact sequence of pixels {i} can be a simple function of iteration k, or can incorporate random sequencing or other patterns.

The classic ICD equations must be modified to extend to EDCT. For simplicity, this disclosure presents equations below for the case of two materials having multiple measurements. However, the equations can be extended in a straightforward manner to N materials with M measurements, although the physical basis for using more than two materials will not be discussed herein (e.g., the presence of K-edges in the attenuation spectra). To begin, the measurement functionals are defined. Let Equation (4) be:

$$F_k(a,b) = \int_E S_k(E) e^{-a\mu_a(E) - b\mu_b(E)} dE. \quad (4)$$

where E denotes energy, k corresponds to "bin number" or "spectrum number," $\mu_a(E)$ is the mass attenuation coefficient (MAC) for material a as a function of energy, and similarly $\mu_b(E)$ is the MAC for material b. These two quantities should have units of reciprocal density-lengths gcm$^{-2}$. The quantity $S_k(E)$ represents the effective spectrum for bin k, and in the case of an energy integrating detector includes premultiplication by the detector absorption profile and the energy weighting term. These measurement functions can also be tabulated to save on computation, or the integrals of E appropriately sampled.

In practice, the measurements are normalized based on a blank and offset scan, and use a logarithm (with additional beam hardening correction in an attempt to map $F_k(a,b) \rightarrow a\mu_a + b\mu_b$. Thus, the following functions of Equation (5) are the most interesting:

$$\hat{f}_k(a,b) = -\log \frac{\int_E S_k(E) e^{-a\mu_a(E) - b\mu_b(E)} dE}{\int_E S_k(E) dE} \quad (5)$$

The two partial derivatives of $f_k$ with respect to each of its arguments are noted in Equation (6) and Equation (7) for later use:

$$\hat{f}_k^a(a,b) = \frac{\partial f_k(a,b)}{\partial a} = \frac{\int_E S_k(E) e^{-a\mu_a(E) - b\mu_b(E)} \mu_a(E) dE}{F_k(a,b)} \quad (6)$$

and $$\hat{f}_k^b(a,b) = \frac{\partial f_k(a,b)}{\partial a} = \frac{\int_E S_k(E) e^{-a\mu_a(E) - b\mu_b(E)} \mu_b(E) dE}{F_k(a,b)} \quad (7)$$

Experiments looked at power series expansions of the type given by Equation (8):

$$f_k(a,b) \approx \sum_m a^{p_m} b^{q_m} c_m \quad (8)$$

but other approaches (e.g. piecewise models, spline fits, etc. are feasible). Note that the results described in this disclosure used the full calculation expressions from equations (6), (7) and (8).

Additionally, the system model A is defined very generally as a linear operator between the pixel values (densities in the EDCT case) and the integrated density-modulated path lengths. With this in mind, the following two equations may be defined by Equation (9) and Equation (10):

$$l_a(j) = \sum_i A_{i,j} x_i^a \quad (9)$$

and $$l_b(j) = \sum_i A_{i,j} x_i^b \quad (10)$$

where $s_a^j$ and $x_b^j$ are the densities of material a and b present in pixel j, and $A_{i,j}$ is the contribution to sinogram element j from pixel i. Note that the same system model is used for both materials. This commonality is in fact a simplification and is not required in practice. Thus the use of different geometries for the system model (to capture dual kVP acquisitions at slightly different sets of view angles, for example) is entirely feasible within this context.

In the absence of detector effects, the measurement equations are then given by Equation (11) and Equation (12):

$$y_k(j) = f_k(l_a(j), l_b(j)) \quad (11)$$

$$= f_k\left(\sum_i A_{i,j} x_i^a, \sum_i A_{i,j} x_i^b\right) \quad (12)$$

Note that this is a nonlinear equation, despite the logarithmic normalization unless the energy integrals collapse to the monochromatic case.

In the monoenergetic case (say $S_k(E) = \sigma_k \delta(E-E_0)$), which yields Equation (13), Equation (14), and Equation (15):

$$f_k(a,b) = -\log \frac{\sigma_k e^{-a\mu_a(E)-b\mu_b(E)} dE}{\sigma_k} \quad (13)$$

$$= -\log e^{-a\mu_a(E_0)-b\mu_b(E_0)} \quad (14)$$

$$= a\mu_a(E_0) + b\mu_b(e_0) \quad (15)$$

This reduction to a system of linear equations is an elegant way to approach EDCT.

There are many ways to extend Equation (1) to EDCT in the full polychromatic case. One successful new approach is to linearize the measurement equations about the current operating point, and then solve the resulting linear equations in a least squares sense or a PWLS sense, as the case may be. If the result is approximates the correct solution (i.e., yields a good initial estimate provided a good start), the linearization can even be fixed up front.

More explicitly, with a small perturbation of size $\alpha$ in material a, and size $\beta$ in material b for pixel i0, the measurement equations with the appropriate substitution become Equation (16) and Equation (17):

$$\hat{y}_k^{\alpha,\beta}(j) = f_k\left(\sum_i A_{i,j}(x_i^a + \alpha \delta_{i_0}), \sum_i A_{i,j}(x_i^b + \beta \delta_{i_0})\right) \quad (16)$$

$$\approx f_k(l_a(j), l_b(j)) + \alpha A_{i_0,j} \dot{f}_k^a(l_a(j), l_b(j)) + \beta A_{i_0,j} \dot{f}_k^b(l_a(j), l_b(j)) \quad (17)$$

where the approximation is valid to within terms of second and higher order in $\alpha, \beta$.

A standard residual term (with the measurement weighting functions suppressed for notational convenience) is Equation (18):

$$J(\alpha, \beta) = \sum_k \sum_j \left(b_k(j) - \hat{y}_k^{\alpha,\beta}(j)\right)^2, \quad (18)$$

but leads to a multidimensional nonlinear optimization problem. With the linearization in place, a simple quadratic problem results in Equation (19):

$$\tilde{J}(\alpha, \beta) = \sum_k \sum_j (b_k(j) - f_k(l_a(j), l_b(j)) - \quad (19)$$

$$\alpha A_{i_0,j} \dot{f}_k^a(l_a(j), l_b(j)) - \beta A_{i_0,j} \dot{f}_k^b(l_a(j), l_b(j)))^2$$

By inspection, the solution for the values of $\alpha, \beta$ that minimize Equation (19) can be written using the normal equations (or, alternatively, by taking the partial derivatives of Equation (12) with respect to $\alpha, \beta$ and setting them to zero). To that end, the following quantities can be defined as Equation (20), Equation (21), Equation (22), Equation (23), and Equation (24):

$$c_{aa} = \sum_k \sum_j A_{i_o,j}^2 \dot{f}_k^a(l_a(j), l_b(j))^2 \quad (20)$$

$$c_{bb} = \sum_k \sum_j A_{i_o,j}^2 \dot{f}_k^b(l_a(j), l_b(j))^2 \quad (21)$$

$$c_{a,b} = \sum_k \sum_j A_{i_o,j}^2 \dot{f}_k^a(l_a(j), l_b(j)) \dot{f}_k^b(l_a(j), l_b(j)) \quad (22)$$

$$d_a = \sum_k \sum_j A_{i_o,j} \dot{f}_k^a(l_a(j), l_b(j))[b_k(j) - f_k(l_a(j), l_b(j))] \quad (23)$$

$$d_b = \sum_k \sum_j A_{i_o,j} \dot{f}_k^b(l_a(j), l_b(j))[b_k(j) - f_k(l_a(j), l_b(j))] \quad (24)$$

As this set of equations indicates, the residual is effectively backprojected into the two component pixels using a derivative weighted backprojection ($d_a, d_b$, and the curvature of the underlying quadratic is similarly computed by backprojecting the square or the derivative components and the cross product of the derivative components ($c_{aa}, c_{ab}, c_{bb}$). Once $c_{aa}, c_{ab}, c_{bb}, d_a, d_b$ have been calculated, the optimal choices of $\alpha, \beta$ to minimize Equation (19) are given by the solution or the following simple 2×2 matrix equation (25):

$$\begin{bmatrix} c_{aa} & c_{ab} \\ c_{ab} & c_{bb} \end{bmatrix} \begin{bmatrix} \alpha \\ \beta \end{bmatrix} = \begin{bmatrix} d_a \\ d_b \end{bmatrix} \quad (25)$$

or in closed form, as Equation (26) and Equation (27):

$$\alpha = \frac{c_{bb} d_a - c_{ab} d_b}{c_{aa} c_{bb} - c_{ab}^2} \quad (26)$$

$$\beta = \frac{c_{aa} d_b - c_{ab} d_a}{c_{aa} c_{bb} - c_{ab}^2} \quad (27)$$

In the case of priors these equations have to be modified to account for the change in curvature induced by the penalty function, but the extension is straightforward. Similarly the incorporation of statistical information in the form of data weighting terms into the inner products is also quite straightforward: one simply replaces $A_{i_0,j} \rightarrow A_{i_0,j} W_j$, where $W_j$ is the reciprocal variance (or some other measure of uncertainty) of the jth sinogram measurement.

The size of this system of equations depends on the number of component images (e.g., materials) being used in the decomposition. If three materials are desired, then a 3×3 system of equations can be derived, and so on (although for larger systems, direct solution of the quadratic equations may be undesirable or infeasible). Note that the dependence on the number of "bins" is fairly trivial. New bins of information can be easily added or removed in a ray-dependent fashion simply through the summations in (18).

The method 100 described above has been implemented for the case of three bins k∈{1, 2, 3}, although the code is completely general in the number of bins that are used in the reconstruction. In an embodiment system model $A_{i,j}$ the distance-driven projector backprojector, modified for efficient calculations in an ICD loop is chosen.

In practice, initializing with a flat field of all zeros for both images may not produce useful final images. This result is not entirely surprising, given the sensitivity of ICD to the initial estimate. As discussed previously with respect to FIGS. 3 and 5, this result may be overcome by applying standard decomposition techniques (i.e., deterministic material decomposition algorithms) combined with filtered backprojection and use the resulting component images as initial estimates.

The current path length estimates about which linearization occurs may be obtained in two ways: directly from multi-spectral acquisition data via material decomposition methods in the projection domain; and alternatively, by re-projecting estimates of component images.

As used herein, an element or step recited in the singular and proceeded with the word "a" or "an" includes plural elements or steps, unless exclusion of such plural elements or steps is explicitly recited. Furthermore, references to "an embodiment" include the existence of additional embodiments that also incorporate the recited features unless exclusion of such additional embodiments is explicitly recited.

The components and arrangements of the new method 100 of extending ICD to handle material decomposition ("MD") for multi-energy CT acquisitions, shown and described herein are illustrative only. Additionally, the order or sequence of any process or method steps may be varied or re-sequenced according to alternative embodiments. Although only a few embodiments of the new method 100 of extending ICD to handle material decomposition ("MD") for multi-energy CT acquisitions have been described in detail, those skilled in the art who review this disclosure will readily appreciate that substitutions, modifications, changes and omissions may be made in the design, operating conditions and arrangement of the preferred and other exemplary embodiments without departing from the spirit of the embodiments as expressed in the appended claims. Accordingly, the appended claims are intended to include all such substitutions, modifications, changes and omissions.

What is claimed is:

1. A method of iterative reconstruction, the method comprising:
   decomposing an energy-discriminating computed tomography ("EDCT") image onto a fixed set of basis components to produce a set of images; and
   performing a sequence of iterations on the set of images, wherein the sequence of iterations includes
   fixing all but one image pixel at an estimated scalar pixel value;
   varying at least one component value of the one image pixel, wherein a number of component values depends on a number of images in the set of images;
   solving a system of linear equations to obtain at least one updated component value of the one image pixel; and
   replacing the at least one component value of the one image pixel with the at least one updated component value.

2. The method of claim 1, further comprising:
   adjusting the at least one updated component value based on prior information about the one image pixel and its component composition.

3. The method of claim 1, further comprising:
   iterating over all image pixels until convergence.

4. The method of claim 3, further comprising:
   displaying an optimized, converged image.

5. The method of claim 1, further comprising, after the step of varying at least one component value of the one image pixel:
   replacing an original (nonlinear) system model with a system model that is linear with respect to the component value being varied.

6. A computed tomography system for iterative reconstruction, comprising:
   a multi-spectral x-ray source;
   a detector positioned to receive multi-spectral acquisition data from the multi-spectral x-ray source;
   a computer processor configured to:
       decompose an energy-discriminating computed tomography ("EDCT") image onto a fixed set of basis components to produce a set of images;
       perform a sequence of iterations on the set of images, wherein for each iteration the computer processor is further configured to:
           fix all but one image pixel at an estimated scalar pixel value;
           vary at least one component value of the one image pixel, wherein a number of component values depends on a number of images in the set of images;
           solve from a system of linear equations to obtain at least one updated component value of the one image pixel; and
           replace the at least one component value of the one image pixel with the at least one updated component value.

7. The computed tomography system of claim 6, wherein the computer processor is further configured to:
   iterate over all image pixels until convergence.

8. The computed tomography system of claim 7, wherein the computer processor is further configured to:
   display an optimized, converged image.

* * * * *